(12) United States Patent
Murakami et al.

(10) Patent No.: US 11,903,873 B2
(45) Date of Patent: Feb. 20, 2024

(54) INFUSION PIPE (71) Applicant: MANI, Inc., Utsunomiya (JP)

(72) Inventors: Etsuo Murakami, Utsunomiya (JP); Masahiro Takano, Utsunomiya (JP)

(73) Assignee: MANI, INC., Utsunomiya (JP)

(*) Notice: Subject to any disclaimer, the term of this patent is extended or adjusted under 35 U.S.C. 154(b) by 111 days.

(21) Appl. No.: 16/642,366

(22) PCT Filed: Aug. 29, 2018

(86) PCT No.: PCT/JP2018/031898
§ 371 (c)(1),
(2) Date: Feb. 26, 2020

(87) PCT Pub. No.: WO2019/044883
PCT Pub. Date: Mar. 7, 2019

(65) Prior Publication Data
US 2020/0179166 A1 Jun. 11, 2020

(30) Foreign Application Priority Data
Aug. 30, 2017 (JP) .................. 2017-165798

(51) Int. Cl.
A61F 9/00 (2006.01)
(52) U.S. Cl.
CPC .................. A61F 9/0017 (2013.01)
(58) Field of Classification Search
CPC ............ A61F 9/0017; A61F 9/007; A61F 2009/0087; A61F 9/00736; A61F 9/00745;
(Continued)

(56) References Cited

U.S. PATENT DOCUMENTS 4,953,594 A * 9/1990 Von Berg .............. G05D 23/27
251/126
4,959,049 A * 9/1990 Smirmaul .......... A61F 9/00745
606/161

(Continued)

FOREIGN PATENT DOCUMENTS

JP 2015066199 A 4/2015
KR 1020150073043 A 6/2015

(Continued)

OTHER PUBLICATIONS

Yuki, Takehiko, WO2016035788A1 (Google Patents Translation) (Year: 2016).*

(Continued)

Primary Examiner — Nicholas J. Weiss
Assistant Examiner — Brandon W. Levy
(74) Attorney, Agent, or Firm — Isshiki & Partners; Joseph P. Farrar (57) ABSTRACT An infusion pipe capable of achieving a flow rate higher or the same as that of a conventional product, and of easily joining to a cannula attached to an eyeball. The infusion pipe of the present invention is used in an ophthalmic operation with the infusion pipe joined to a cannula attached to an eyeball, and includes an insertion part to be inserted, at the time of joining to the cannula, inside a cannula piercing part, which is a part of the cannula for piercing the eyeball. A cross-section of the insertion part is an arc shape from which a part of a circle is cut out.

1 Claim, 6 Drawing Sheets (58) Field of Classification Search
CPC ....... A61F 2009/00887; A61M 3/0279; A61M 39/10; A61M 2039/1072; A61M 2205/197; A61M 2039/1077; A61M 2205/195; A61M 2039/107777; A61M 25/003; A61M 25/0067; A61M 25/0068; A61M 25/0069; A61M 25/007; A61M 25/0071; A61M 2025/0073; A61M 5/3286; A61B 17/00; A61B 17/3421; A61B 2017/00477; A61B 17/320016; A61B 17/3462; A61B 2217/005; A61J 1/2048; A61J 1/2051; A61J 1/2055; A61J 1/1475; A61J 1/1481; A61J 1/1487; A61J 1/10

See application file for complete search history.

(56) References Cited

U.S. PATENT DOCUMENTS

| | | | | |
|---|---|---|---|---|
| 4,976,691 | A * | 12/1990 | Sahota | A61M 25/0068 604/103.05 |
| 6,193,697 | B1 * | 2/2001 | Jepson | A61M 5/162 604/201 |
| 2006/0089526 | A1 | 4/2006 | Chen et al. | |
| 2008/0177239 | A1 * | 7/2008 | Li | A61B 17/3421 604/264 |
| 2009/0076463 | A1 * | 3/2009 | Attinger | A61B 17/3421 604/264 |
| 2009/0234292 | A1 * | 9/2009 | Di Nardo | A61B 17/3462 604/167.01 |
| 2011/0152775 | A1 * | 6/2011 | Lopez | A61F 9/007 604/167.01 |
| 2015/0272780 | A1 | 10/2015 | Carriazo | |
| 2016/0213511 | A1 | 7/2016 | Murakami et al. | |

FOREIGN PATENT DOCUMENTS

| | | | | |
|---|---|---|---|---|
| WO | WO-9629112 A1 * | 9/1996 | ........ | A61M 39/0208 |
| WO | WO-2016035788 A1 * | 3/2016 | ............. | A61J 15/00 |

OTHER PUBLICATIONS

International Search Report (ISR) for Application No. PCT/JP2018/031898 dated Nov. 20, 2018.
Translation of the ISR for Application No. PCT/JP2018/031898 dated Nov. 20, 2018.
Written Opinion of the International Search Authority for Application No. PCT/JP2018/031898 dated Nov. 20, 2018.

* cited by examiner

PRIOR ART

FIG. 6

INFUSION PIPE

CROSS REFERENCE TO RELATED APPLICATIONS

The present application is a national phase entry under 35 U.S.C. § 371 of International Application No. PCT/JP2018/031898, filed on Aug. 29, 2018, which claims priority from Japanese Application No. 2017-165798, filed on Aug. 30, 2017, the entire disclosures of which are hereby incorporated by reference herein.

TECHNICAL FIELD

The present invention relates to an infusion pipe used in an ophthalmic operation with the infusion pipe joined to a cannula attached to an eyeball.

BACKGROUND ART

Vitreous surgery is surgery for cutting and removing a gelatinous vitreous body within the eyeball or a proliferative membrane formed on the retina through degeneration of the vitreous body. Such an ophthalmic operation is performed while irrigating inside the eyeball with water using an infusion cannula.

Figure 5:
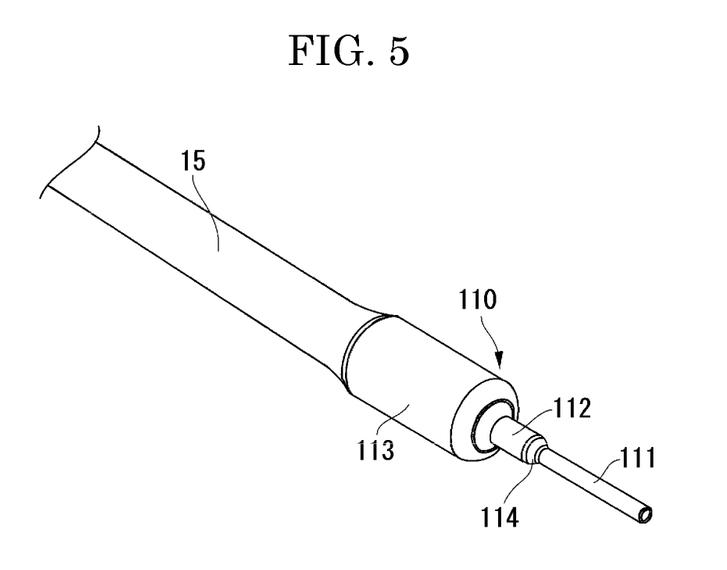
FIG. 5 is an oblique view of an infusion pipe of a conventional product.
Figure 6:
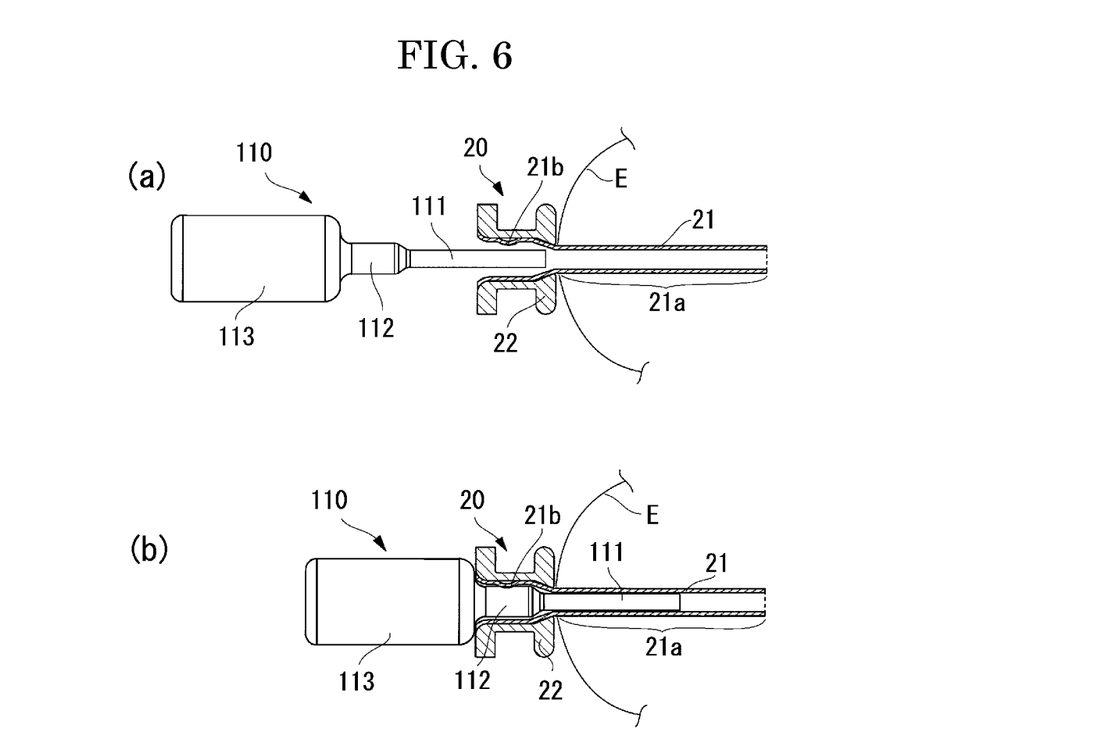

The infusion cannula has a tube allowing the perfusing water to pass through, and an infusion pipe connecting the tube and the cannula. FIG. 5 is an oblique view of an infusion pipe of a conventional product. FIG. 6 is a diagram describing joining of a cannula and an infusion pipe of the conventional product, wherein FIG. 6(a) illustrates a state during the joining process and FIG. 6(b) illustrates the state after the joining process. Note that illustration of a tube 15 is omitted from FIG. 6.

An infusion pipe 110 is used with it joined to a cannula 20 that is attached to an eyeball E (see Patent Document 1, for example). The cannula 20 has a metal cannula pipe 21 fit into a cannula base 22 made of resin. In the cannula pipe 21, a portion fit into the cannula base 22 is a cannula joining part 21b, and a portion piercing in the eyeball E is a cannula piercing part 21a.

The shape of the cannula piercing part 21a is a tubular form having a constant diameter. The shape of the cannula joining part 21b has a larger diameter than that of the cannula piercing part 21a and has an inward protrusion, and when joining it to the infusion pipe 110 via this protrusion, the side part of a joining part 112 is pressed and secured. Moreover, when the cannula piercing part 21a is pierced in the eyeball E, the cannula base 22 acts as a stopper.

The infusion pipe 110 has an insertion part 111 to be inserted in the cannula piercing part 21a, the joining part 112 to be pressed and secured by the protrusion of the cannula joining part 21b, and a base part 113 connected to the tube 15. Note that the cross-section of the insertion part 111 has a circular shape. Moreover, since the joining part 112 has a larger diameter than that of the insertion part 111, the boundary therebetween is connected by a connecting part 114.

While the insertion part 111 needs to be inserted in the cannula pipe 21, as illustrated in FIG. 6(a) and FIG. 6(b), when joining together the infusion pipe 110 and the cannula 20, it is not easy to insert the insertion part 111 of the infusion pipe 110 until inside the thin cannula pipe 21 that is pierced in the eyeball E. Furthermore, the cannula piercing part 21a is made for piercing the eyeball E, and can thus not be too thick. As a result, there is a problem that the water passing through the insertion part 111 of the infusion pipe 110, which is thinner than the cannula piercing part 21a, consequently becomes a small amount.

PRIOR ART DOCUMENTS

Patent Documents

[Patent Document 1] JP 2015-66199A

DISCLOSURE

Problem to be Solved

In light of this problem, the present invention aims to provide an infusion pipe that can acquire a higher flow rate than the infusion pipe of a conventional product, and easily carry out joining to a cannula that is attached to an eyeball.

Solution to the Problem

The infusion pipe of the present invention, in order to reach the above aim, is an infusion pipe used in an ophthalmic operation with the infusion pipe joined to a cannula attached to an eyeball, including an insertion part to be inserted, at the time of joining to the cannula, inside a cannula piercing part, which is a part of the cannula for piercing the eyeball. A cross-section of the insertion part is an arc shape from which a part of a circle is cut out.

Moreover, arc height of the cross-section of the insertion part should be 30% or greater and 90% or less of the outer diameter of a virtual circular cross-section that is intact.

Advantageous Effect

According to the infusion pipe of the present invention, there are beneficial results that a higher flow rate than that with an infusion pipe having a circular cross-section may be achieved, and joining to a cannula may be easily carried out.

BRIEF DESCRIPTION OF DRAWINGS

FIG. 2 is a diagram describing joining of the infusion pipe of the present invention and a cannula, wherein FIG. 2(a) illustrates a state during the joining process and FIG. 2(b) illustrates the state after the joining process;

FIG. 6 is a diagram describing joining of a cannula and an infusion pipe of the conventional product, wherein FIG. 6(a) illustrates a state during the joining process and FIG. 6(b) illustrates the state after the joining process.

DESCRIPTION OF EMBODIMENTS

An embodiment according to the present invention is described below with reference to accompanying drawings.

Figure 1:
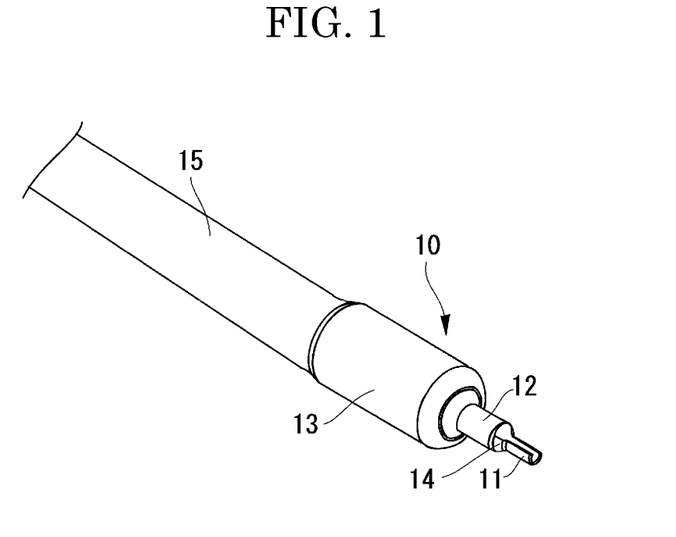
FIG. 1 is an oblique view of an infusion pipe of the present invention.
Figure 2:
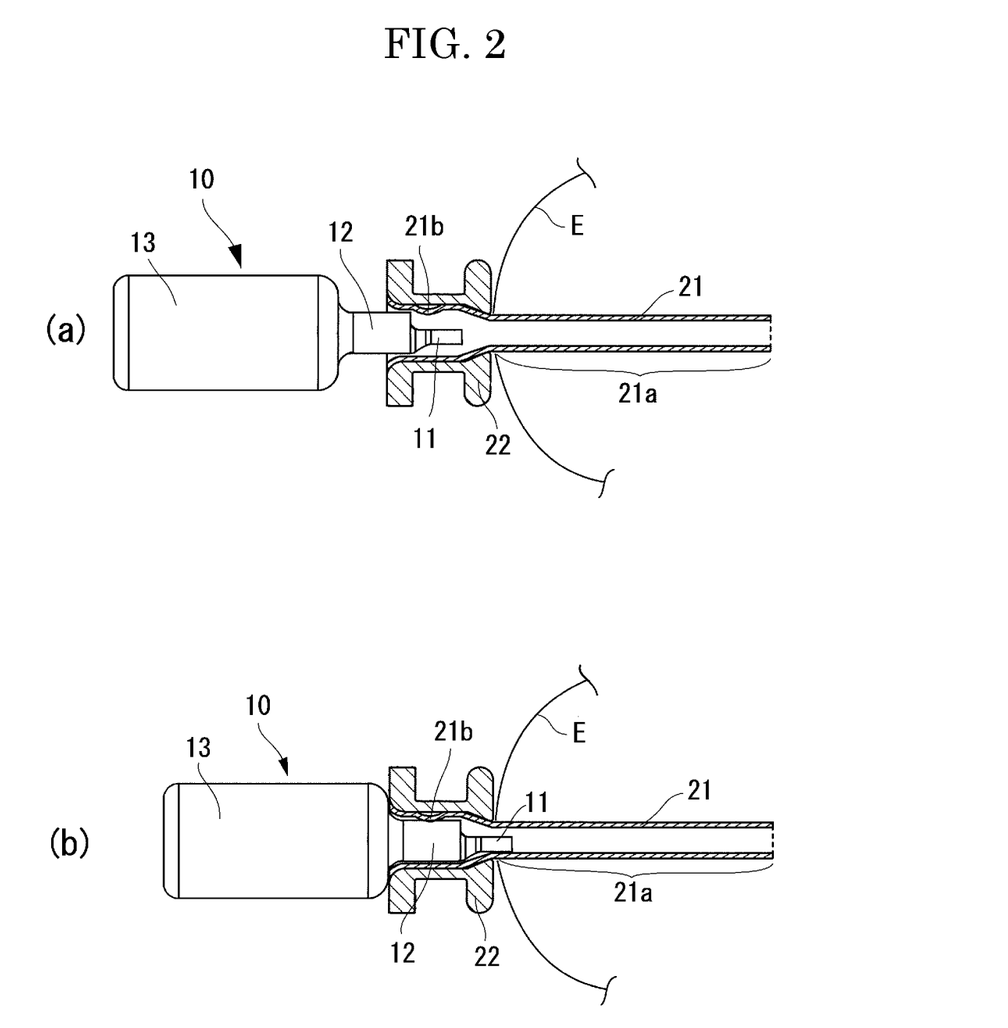

FIG. 1 is an oblique view of an infusion pipe of the present invention. In addition, FIG. 2 is a diagram describing joining of the infusion pipe of the present invention and a cannula, wherein FIG. 2(a) illustrates a state during the joining process and FIG. 2(b) illustrates the state after the joining process. A cannula 20 for joining an infusion pipe 10 is made by fitting a metal cannula pipe 21 into a resin cannula base 22, as with the conventional cannula. Moreover, the cannula pipe 21 has a portion fit in the cannula base 22 as a cannula joining part 21b, and a portion pierced in an eyeball E as a cannula piercing part 21a.

The basic configuration of the infusion pipe 10 similarly to the conventional pipe has an insertion part 11 to be inserted inside the cannula piercing part 21a, the joining part 12 to be pressed and secured by the cannula joining part 21b, and a base part 13 connected to a tube 15. Moreover, since the joining part 12 has a larger diameter than that of the insertion part 11, the boundary therebetween is connected by a connecting part 14 which is shorter than the insertion part 11.

Difference between the infusion pipe 10 of the present invention and the infusion pipe of the conventional product is that the cross-section of the insertion part 11 is not a closed circle, but is an arc shape with a part of the circle cut out. Furthermore, axial length of the insertion part 11 is shorter than that of the insertion part of the conventional product. For example, the length of the insertion part 11 may be approximately the same as length of the joining part 12 or it may be shorter.

Since the cannula piercing part 21a that pierces the eyeball E has a small diameter, and there is hardly any gap between the inner diameter of the cannula piercing part 21a and the outer diameter of the insertion part 11 of the infusion pipe 10, the insertion process becomes much easier than with the conventional product if the cross-section of the insertion part 11 is an arc shape and shorter.

Moreover, since it is an open channel if the cross-section of the insertion part 11 is an arc shape, the flow rate of irrigating water is thus higher than a pipe line of the conventional product. Furthermore, if the insertion part 11 is shorter, resistance of the channel on the flowing water becomes smaller, and flow rate is increased.

Figure 3:
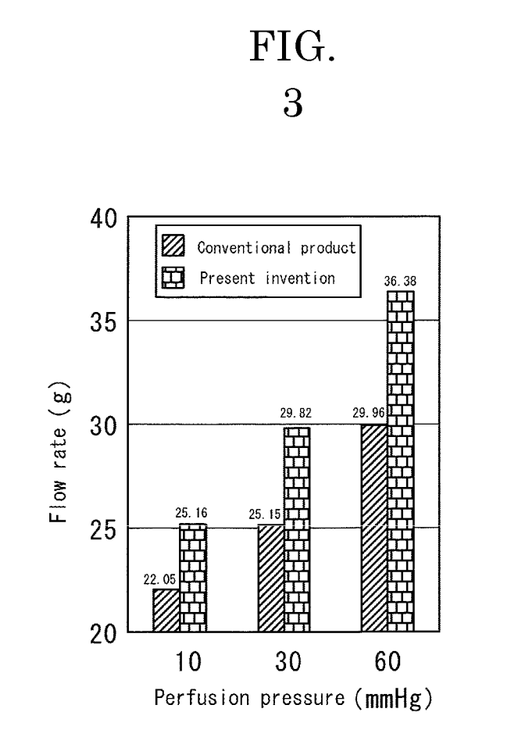
FIG. 3 is a graph comparing the flow rate per minute with a conventional product and that with the infusion pipe of the present invention.

FIG. 3 is a graph comparing flow rate (g) per minute with a conventional product and that with the infusion pipe of the present invention. The conventional product is an infusion pipe having a cross-section that is circular having an outer diameter of 0.43 mm. Meanwhile, the present invention is an infusion pipe having an insertion part cross-section that is an arc shape resulting from leaving a 0.29 mm-high arc from a virtual circular cross-section having an outer diameter of 0.43 mm. Note that a circular cross-section without a cut-out portion is set as the virtual circular cross-section. Moreover, arc height is vertical height from the lower edge of the arc to the ends of the arc when the arc shape is positioned such that the upper side is open to make it bilaterally symmetrical. That is, the insertion part of the infusion pipe of the present invention used for this flow rate comparison has a cross-section with approximately 67% (=0.29/0.43*100) of the arc height of the virtual circular cross-section.

It is understood from the flow rate comparison graph of FIG. 3 that when the infusion pipe of the present invention is used even with a perfusion pressure of any one of 10 mmHg, 30 mmHg, or 60 mmHg, the flow rate is approximately 10 to 20% higher than that of the conventional product. Therefore, as with the present invention, a result allowing increase in flow rate is achieved if the cross-section of the infusion pipe is made an arc shape.

Figure 4:
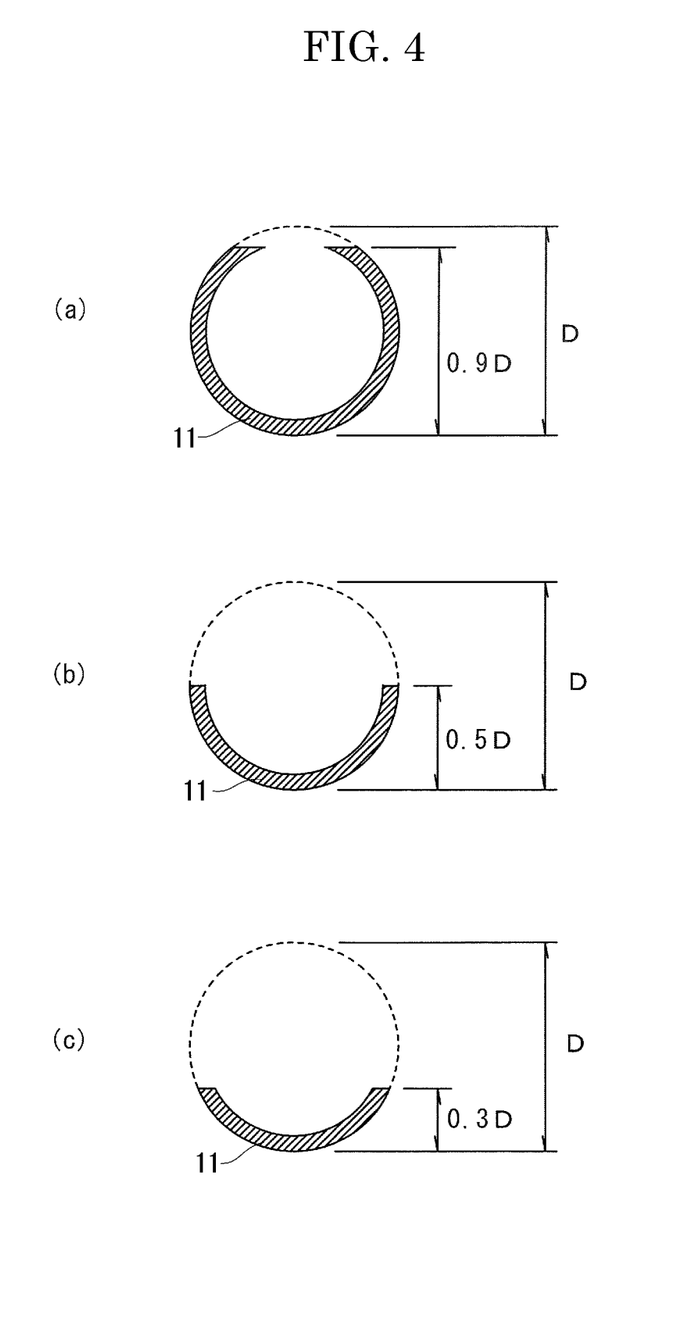
FIG. 4 is a cross-section of an insertion part of the infusion pipe of the present invention.

Next, an allowable range of arc height of an insertion part cross-section of the infusion pipe is determined. FIG. 4 is a cross-section of the insertion part of the infusion pipe of the present invention. FIG. 4(a) illustrates an arc height of 0.9 times an outer diameter D of a virtual circular cross-section, FIG. 4(b) illustrates a height of 0.5 times (semicircle) the same, and FIG. 4(c) illustrates a height of 0.3 times the same.

Arc heights of the cross-section of the insertion part 11 of the infusion pipe 10 according to the present invention are limited within the range of an upper limit and a lower limit illustrated in FIG. 4(a) and FIG. 4(c), respectively. This is because if the arc height is greater than that of FIG. 4(a) (arc height: 0.9D), the cross-section would be hardly different from a circle when looking at the cross-sectional shape, and the result of increase in flow rate cannot be expected. Moreover, if the arc height is lower than that of FIG. 4(c) (arc height: 0.3D), the cross-section would be almost flat, and there would be no meaning in provision of the insertion part 11.

Furthermore, flow rate when arc height is changed is tested and studied. The test has compared flow rates with 11 kinds of infusion pipes having an outer diameter of 0.43 mm of the virtual circular cross-section, and arc heights from 0 mm (0%) to 0.43 (100%) at a pitch of approximately 0.04 mm (approximately 10%). The test is carried out at a pressure of 60 mmHg, measuring the flow rate (g) per minute. As a result, while there are some errors, it is confirmed that as the arc height increases, the flow rate tends to decrease, as expected. Looking at the flow rate at each arc height relative to flow rate for the arc height of 0 mm (0%) as a standard, flow rate for the arc height of 0.43 mm (100%) is approximately 88% of the flow rate for the arc height of 0 mm (0%), while in the case of other arc heights, flow rate of 90% or greater of the flow rate for the arc height of 0 mm (0%) is secured. That is, it is confirmed that if the arc height is set to 90% or less of the outer diameter D of the virtual circular cross-section, the flow rate may be increased more than that with the conventional infusion pipe, and a constant flow rate may be secured. Note that the flow rate tends to increase the closer it approaches the arc height of 0 mm; however, as described before, since the cross-section becomes nearly flat when the arc height is made lower than that in FIG. 4(c) (arc height 0.3D), thereby losing the meaning of providing the insertion part 11, the lower limit of arc height is set to 30% of the outer diameter of the virtual circular cross-section. As a result, the allowable range of arc height according to the present invention is set to 30% or greater and 90% or less of the outer diameter of the virtual circular cross-section.

Note that, when paying attention to flow rate only, while the arc height of the insertion part 11 is preferably smaller than that of the semicircle since flow rate increases the lower the arc height, there are cases where the arc height is preferably larger than that of the semicircle when also concurrently considering stability etc. of the infusion pipe 10 when joined to the cannula.

Since the gap between the cannula piercing part 21a and the insertion part 11 is larger when, for example as illustrated in FIG. 4(c), the arc height of the insertion part 11 is smaller than the semicircle, there is concern that the infusion pipe 10 joined to the cannula is unstable. Moreover, with such a shape, since the end of the insertion part 11 is nearly pointed, there is concern that the end is caught when inserted in the cannula pipe.

Meanwhile, when the arc height of the insertion part 11 is greater than that of the semicircle, as in FIG. 4a, the gap between the cannula piercing part 21a and the insertion part 11 is smaller, and the infusion pipe 10 joined to the cannula is thus easily made stable.

If increasing the flow rate is considered most important, making the arc height of the insertion part 11 as low as possible is preferred; however, considering workability and stability at the time of joining, a certain degree of arc height should be secured. Accordingly, when making a general judgment, if the cross-section of the infusion pipe 10 is made to have an arc height of 30 to 90% of the outer diameter of the virtual circular cross-section without any cut-out portion, it is considered able to easily join to the cannula while increasing the flow rate without any problem, and if securing greater stability at the time of joining is desired, it should be made 50% or greater of the outer diameter of the virtual circular cross-section.

EXPLANATION OF REFERENCE NUMERALS

10: Infusion pipe
11: Insertion part
12: Joining part
13: Base part
14: Joint
15: Tube
20: Cannula
21: Cannula pipe
21*a*: Cannula piercing part
21*b*: Cannula joining part
22: Cannula base
E: Eyeball

The invention claimed is:

1. An infusion pipe used in an ophthalmic operation, comprising:
   an insertion part to be inserted inside a cannula joining part continuous with a cannula piercing part of a cannula for piercing an eyeball;
   a joining part having a diameter larger than a diameter of the insertion part, and configured to be crimped and secured by an inward protrusion formed in an inner surface of the cannula joining part of the cannula when the insertion part is inserted into the cannula; and
   a connecting part that connects the joining part and the insertion part,
   wherein the insertion part is shorter than the joining part,
   wherein a cross-section of the insertion part is an arc shape from which a part of a circle is cut out,
   wherein an arc height of the cross-section of the insertion part is 50% or greater and 70% or less of an outer diameter of a virtual circular cross-section that is intact, and
   wherein the infusion pipe is connected to a tube allowing perfusing water to pass therethrough.

* * * * *